(12) United States Patent
Plochocka

(10) Patent No.: US 7,048,912 B2
(45) Date of Patent: May 23, 2006

(54) POLYMERIC DELIVERY AND RELEASE SYSTEMS FOR ORAL CARE ACTIVES

(75) Inventor: Krystyna Plochocka, Scotch Plains, NJ (US)

(73) Assignee: ISP Investments Inc., Wilmington, DE (US)

( * ) Notice: Subject to any disclaimer, the term of this patent is extended or adjusted under 35 U.S.C. 154(b) by 340 days.

(21) Appl. No.: 10/461,796

(22) Filed: Jun. 13, 2003

(65) Prior Publication Data

US 2004/0253188 A1 Dec. 16, 2004

(51) Int. Cl.
*A61K 8/00* (2006.01)
(52) U.S. Cl. ............................ 424/49; 424/53; 424/55; 433/215; 433/216; 433/217.1; 524/558; 524/563
(58) Field of Classification Search ................ 424/49
See application file for complete search history.

(56) References Cited

U.S. PATENT DOCUMENTS 3,751,561 A * 8/1973 Wildi et al. .................. 424/48
5,700,478 A * 12/1997 Biegajski et al. ............ 424/434
6,315,987 B1 * 11/2001 Plochocka .................... 424/49
2005/0003448 A1 * 1/2005 Zhao et al. .................. 435/7.1

OTHER PUBLICATIONS

Bowles et al. Design, Formulation, and Evaluation of Isocyanatocrylate Copolymer Dental Adhesives. (1999) John Wiley & Sons, Inc.*

* cited by examiner

*Primary Examiner*—Christopher S. F. Low
*Assistant Examiner*—Michel Graffeo

(74) *Attorney, Agent, or Firm*—Walter Katz; William J. Davis

(57) ABSTRACT

A polymer for use in an oral care composition which includes a monomer repeat unit containing an active material covalently bonded to a hydrolyzable side group of said monomer unit, and a spacer group positioned between the main chain of said polymer and said hydrolyzable side group, said polymer having a predetermined rapid rate of aqueous hydrolysis to release said active material therefrom.

14 Claims, 1 Drawing Sheet

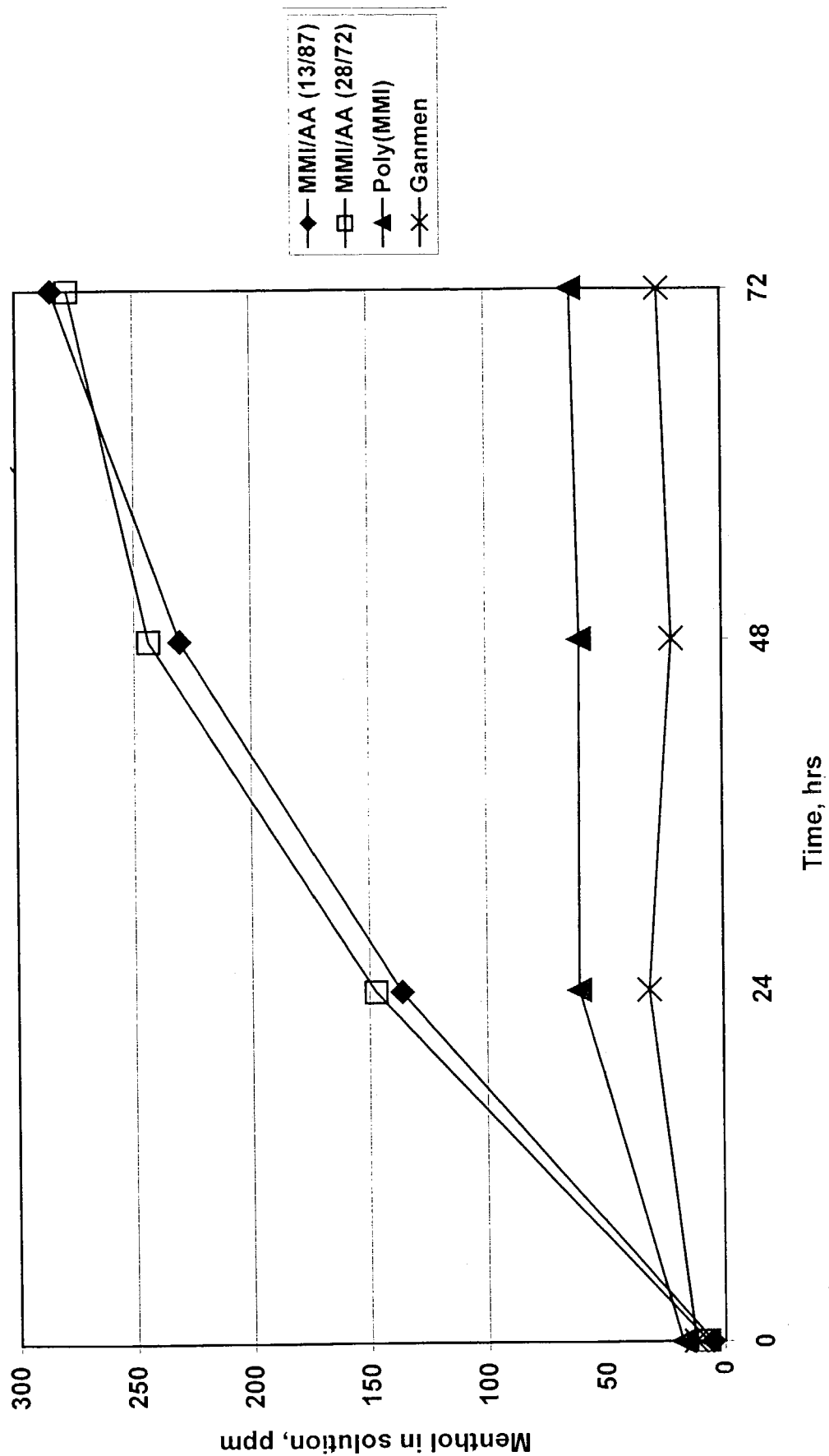

POLYMERIC DELIVERY AND RELEASE SYSTEMS FOR ORAL CARE ACTIVES

CROSS REFERENCE TO RELATED U.S. PATENTS

This application is related to U.S. Pat. Nos. 6,315,987 and 6,464,961, issued to the same applicant and assigned to the same assignee as herein.

BACKGROUND OF THE INVENTION

1. Field of the Invention

This invention relates to oral care compositions, and, more particularly, to a polymer for use in such compositions which has a reactive group therein covalently bonded to an active material, such as a bactericide, flavorant and/or essential oil compound, which bond is readily hydrolyzable in the aqueous condition of the mouth of the user to release the material therein.

2. Description of the Prior Art

Oral care compositions such as dentifrices, denture adhesives, buccal tapes, anti-plaques, mouthwashes, mouthstrips, and chewing gums usually contain one or more added active materials, particularly antimicrobial compounds, e.g. triclosan or thymol, or flavorants, e.g. menthol and thymol, or essential oils. However, these active materials are released immediately after use into the mouth of the user, and, accordingly, are not available at any time thereafter.

On the other hand, the related U.S. Pat. Nos. 6,315,987 and 6,464,961 described a copolymer of maleic anhydride and methyl vinyl ether having e.g. an active menthol group covalently bonded by esterification to the reactive anhydride of the copolymer, which ester group only slowly hydrolyzed in aqueous solution, and thus very little of the active was released at the instant of use.

For these reasons, it is an object of this invention to provide an oral care composition including a polymer which is a delivery system which can release a proportion of the active compound when the polymer is present in the aqueous condition of the mouth, with the rest of the polymer being made available for hydrolysis thereafter.

Another object of the invention is to provide such an oral care composition in which the polymer also is bioadhesive to the teeth and gums of the user.

These and other objects and features of the invention are achieved herein by the provision of a polymer for use in an oral care composition which includes a monomer repeat unit containing an active material covalently bonded to a hydrolyzable side group of the monomer unit, and a spacer group positioned between the main chain of said polymer and the hydrolyzable side group, the polymer having a predetermined rapid rate of aqueous hydrolysis to release the active material therefrom.

IN THE DRAWINGS

The FIGURE is a plot of ppm menthol released vs. time for various polymers and copolymers of the invention.

SUMMARY OF THE INVENTION

What is described herein is a polymer for use in an oral care composition which includes a monomer repeat unit containing an active material covalently bonded to a hydrolyzable side group of the monomer unit, and a spacer group positioned between the main chain of the polymer and the hydrolyzable side group, the polymer having a predetermined rapid rate of aqueous hydrolysis to release said active material therefrom.

More particularly, the polymer can release a significant proportion of the active material within 24 hours of the time the polymer is present in the mouth of the user, the rest undergoing further aqueous hydrolysis thereafter.

Preferably the polymer has a spacer group which is alkylene, carbonate, alkyleneoxy, amino, amido, anhydride, amino acid or alkylene ester, most preferably alkylene, e.g. methylene.

A preferred hydroyzable side group is a carboxylic group which can form an ester or amide with the active material, optionally wherein the monomer repeat unit also includes another carboxylic group.

Suitably, both the side and carboxylic groups can be attached to the same or different carbon atoms in the main polymer chain, preferably to the same carbon atom.

A particularly preferred polymer is one in which the active is present in the side monoester group of itaconic acid.

Suitable active materials include antimicrobial, flavorants or essential oils, e.g. menthol, thymol, triclosan, methyl salicylate and the like. Menthol is preferred.

In a preferred form of the invention, the polymer also includes a comonomer, most preferably a water solubilizing comonomer, e.g. (meth)acrylic acid, itaconic acid, vinyl acetate, a maleate, a fumarate, vinyl pyrrolidone, vinyl caprolactam, methacrylic acid, vinyl amide, alkyl vinyl ether, maleic anhydride, vinyl sulphonic acid, dimethylaminopropyl methacrylic acid or dimethylaminopropyl methacrylamide. Acrylic acid is preferred. Such water soluble copolymers preferably have bio-adhesive properties.

Preferred polymers have an ester group containing the active which can form a 5- or 6-membered anhydride ring with a carboxylic group in the polymer.

The polymers of the invention find particular utility in oral care compositions, such as dentifrice, buccal tapes, denture adhesive, anti-plaque, mouthwashes, mouthstrips, and chewing gum compositions.

DETAILED DESCRIPTION OF THE INVENTION

The polymer of the present invention may be made by reacting a suitable monomer with an active material to form a monomer with a hydrolyzable side group having the active covalently bonded therein, and then polymerizing the reaction product. Alternatively, the monomer may be polymerized first, and then the active material reacted with a side group of the polymerized monomer, to form the desired polymer. Comonomers may be copolymerized with the selected monomer after reaction of the monomer with the active material, or following polymerization of the monomer. Preferably, both monomer and comonomer are polymerized together before or after reaction with the active material.

In accordance with the invention, there is provided herein polymers containing covalently-bound active components which can be used as effective delivery and release systems of such actives in aqueous oral care compositions. Typical active materials include antimicrobial compounds, e.g. triclosan or thymol, or flavorants, e.g. menthol or thymol, or essential oils, e.g. methyl salicylate. These active materials are covalently bound in a side group of the polymer, e.g. by an acid, carboxylate, ester or amide group, which can undergo rapid aqueous hydrolysis in the mouth. Such polymers also can be made by copolymerization of monomers with a comonomer such as (meth)acrylic acid, itaconic acid, vinyl acetate, a maleate, a fumarate, vinyl pyrrolidone, vinyl caprolactam, vinyl sulphonic acid, methacrylic acid, vinyl amide, alkyl vinyl ether, maleic anhydride, dimethylaminopropyl methacrylic acid or dimethylaminopropyl methacrylamide, by esterification of carboxylic or anhydride side groups; or by transesterification of ester groups in a polymer.

The polymer of the invention may be illustrated by the following generic formula:

$$-(CH_2-\underset{\underset{\underset{Z}{|}}{\underset{Y}{|}}}{\underset{X}{|}}{C})-(M)-$$

where:
- X is a spacer group;
- Y is a hydrolyzable side group;
- Z is an active material;
- $-(-CH_2-C-)-$ is the main polymer chain, or repeat unit;
- A is H or a functional group, e.g. carboxylate or carboxylic group, and
- M is an optional comonomer.

Suitable X groups include alkylene, alkyleneoxy, amino, anhydride, carbonate, amino acid or alkylene ester. Alkylene, e.g. methylene is preferred.

Suitable Z groups are active antimicrobial, flavorant or essential oil. Menthol is preferred.

Suitable repeat units of the main polymer chain include alkylene with or without another functional group attached thereto, e.g. carboxylate.

Suitable M comonomers, e.g. (meth)acrylic acid, are present to solubilize the polymer in aqueous solution, generally in an amount up to 95% of the polymer.

A preferred main monomer of the invention is the thymyl or menthyl monoester of itaconic acid ("MI"), whose polymer has the formula:

$-(-CH_2-\underset{\underset{\underset{\underset{R}{|}}{\underset{O}{|}}}{\underset{C=O}{|}}}{\underset{CH_2\ COOH}{|}}{C})_n-$ where R is menthyl or thymyl A preferred copolymer of the invention includes "MI" and acrylic acid repeat units ("MI/AA") having the formula:

$$-(CH_2-\underset{\underset{\underset{\underset{R}{|}}{\underset{C=O}{|}}}{\underset{CH_2}{|}}}{\underset{COOH}{|}}{C})_n-(CH_2-\underset{COOH}{\underset{|}{CH}})_m-$$

Suitably where
n=0.05–0.95; and
m=0.05–0.95.

The mono-menthyl itaconate may be made conveniently by direct esterification in the melt of itaconic anhydride and menthol, as follows:

where ROH is menthol.

Aqueous hydrolysis of the "MMI" copolymer proceeds as follows:

The invention will be described hereinafter with reference to the following examples.

EXAMPLE 1

Monomenthyl Itaconate ("MMI")

A round bottom, 3-neck flask with oil bath, overhead agitator, reflux condenser equipped with drying tube and temperature probe was charged with 46.9 g (0.30 mol) of menthol and 36.7 g (0.33 mol) of itaconic anhydride. The reactants were heated until the ingredients melted (about 80° C.). Then the agitator was turned on and the temperature was held for 4 hrs. Thereafter the temperature was raised to 90° C. and maintained thereat for 5 hrs, whereupon, the contents of the flask became semisolid. The contents of the flask were emptied into the plastic lined glass tray whereupon the material solidified over a few days to a waxy solid. Yield: 73 g. The product was identified as mono-menthyl itaconate by GC-MS, with a trace amount of itaconic anhydride and menthol. The reaction sequence and molecular structure of mono-menthyl itaconate was shown.

EXAMPLE 2

Homopolymerization of Monomenthyl Itaconate (Poly "MMI")

A 1-l Buchi reactor was charged with 15.0 g of monomenthyl itaconate, 3.0 g of Luperox$^R$ 11M75 (t-butyl peroxypivalate—Atofina) as initiator and 200 ml of methyl-t-butyl ether (MTBE) sparged separately with nitrogen. The reactor was sealed and sparged with nitrogen. Agitation was started and the contents were heated to 65° C. The temperature and agitation conditions were maintained for 6 hrs. The reactor then was cooled and left overnight. Then again 1.0 g Luperox$^R$ 11M75 as a booster was added and the reactor was again sparged with nitrogen and reheated with agitation to 75° C. After 6 hrs at that temperature, the reactor was cooled. The contents were a semi-transparent, slightly viscous liquid; it was discharged into a plastic lined glass tray. The liquid was vacuum dried at room temperature until most of the solvent was removed. The resultant glassy product then was ground and dried in a vacuum oven (65° C. for 6 hrs). Yield: 12.4 g of a slightly yellow, fine powder identified by $^{13}$C NMR as the homopolymer of monomenthyl itaconate.

EXAMPLE 3

Copolymerization of Monomenthyl Itaconate and Acrylic Acid ("MMI/AA")

A. MMI/AA (28/72)

A 1-l Buchi reactor was charged with 15.0 g (0.056 mole) of monomenthyl itaconate and 300 ml methyl-t-butyl ether (sparged separately with nitrogen). The reactor was sealed and sparged with nitrogen. The temperature then was raised to 65° C. A solution of 8.1 g of acrylic acid in 50 ml MTBE and 3 g Luperox$^R$ 11M75 in 50 ml MTBE was prepared. Half of the Luperox$^R$ solution was added over a period of 6 hrs. The temperature was maintained for 1 hr and then the reaction was cooled to room temperature and left overnight. Thereafter, the reaction was heated to 65° C. and the remaining half of the solution was fed in over 3 hrs. The temperature then was raised to 75° C. and maintained for 3 hrs. The reactor then was cooled down and the contents were discharged into a plastic lined glass tray. The hazy solution was air dried, followed by vacuum drying. The product was ground yielding 21.3 g of a slightly yellowish powder, identified by $^{13}$C NMR as a copolymer of 28-mole % monomenthyl itaconate and 72-mole % of acrylic acid.

B. MMI/AA (11/89)

Similarly, a copolymer of 11-mole % monomenthyl itaconate and 89-mole % acrylic acid was prepared. Its molecular structure and monomer ratios were confirmed by $^{13}$C NMR. The molecular structure of monomenthyl itaconate/acrylic acid copolymer is given above.

EXAMPLE 4

Copolymerization of Itaconic Anhydride and Acrylic Acid

A 1-l Buchi reactor sparged with nitrogen was charged with 4.48 g (0.038 mole) itaconic anhydride and 450 ml MTBE (separately sparged with nitrogen). The reactor was sealed and heated to 65° C. Then 29.69 g (0.412 mole) of acrylic acid and of a solution of 3.0 g Luperox$^R$ 11M75 in 30 ml MTBE was introduced over a period of 6 hrs. The reactor then was maintained for 1 hr at 65° C., cooled to room temperature and left overnight. Then the reactants were heated to 75° C. and a solution of 2.0 g Luperox$^R$ 11M75 in 20 ml MTBE was fed in over 5 hrs. The reactants were heated to 85° C. and temperature was maintained for 2 hrs. Following this hold time, the reactor was cooled down and discharged. The resulting white slurry was filtered and rinsed at the filter with MTBE. The product was dried under vacuum (65° C., 7 hrs). A fine white powder was obtained. Yield: 21 g of the copolymer containing 8-mole % of itaconic anhydride (by $^{13}$C NMR).

EXAMPLE 5

Esterification of Itaconic Anhydride/Acrylic Acid Copolymer with Menthol (Poly MMI/AA)

The itaconic anhydride/acrylic acid copolymer of Example 4 (10 g) and menthol (5 g) were charged in a sealed glass ampoule. The ampoule then was heated in a 120° C. oil bath for 12 hrs with occasional shaking to distribute the melted menthol. The contents then were ground and extracted with hexane to remove excess menthol. The extracted solids were dried under vacuum (65° C., 7 hrs) and ground. Yield: 10.2 g of a yellowish powder. The FTIR spectrum was similar to that of monomenthyl itaconate/acrylic acid copolymer of Example 3, indicating that esterification of the copolymer with menthol was accomplished.

EXAMPLE 6 (COMPARATIVE)

Esterification of Methyl Vinyl Ether/Maleic Anhydride Copolymer with Menthol ("Gan men")

Gantrez® 903 AN (product of ISP) (15.6 g) powder was blended with 31.2 g menthol crystals in a 250 ml round bottom, 3-neck, sealed flask, with agitator and oil bath. The contents were heated with agitation at 100° C. for 24 hrs. Then the temperature was increased to 120° C. and maintained for 24 hrs. The product was a glassy, yellowish material, which was discharged, ground and extracted with hexane to remove unreacted menthol. The yield of a slightly yellow powder was 21 g.

Aqueous Hydrolysis of Examples 2, 3A, 3B and 6 (FIGURE)

The individual polymers were dissolved in a pH 7 borate buffer after neutralization of 60% of their —COOH groups with NaOH (based on NMR data). The solutions were sealed in GC vials and placed in an oven at 37° C. The vials were withdrawn every 24 hours and tested for free menthol by GC. Plots representing free menthol (ppm) in aqueous solution versus time are shown in the FIGURE. The two upper curves relate to MMI/AA copolymers at 0.5 wt. % in water, and two lower ones relate to Poly(MMI) and Ganmen at 1% in water. The data in the FIGURE show that menthol is released from MMI/AA copolymers about 20 times faster than from the Ganmen control.

Faster release of menthol from MMI polymers than from menthyl ester of methyl vinyl ether/maleic anhydride copolymer (Ganmen) confirms the effect of —$CH_2$— spacer on the rate of release.

While the invention has been described with particular reference to certain embodiments thereof, it will be understood that changes and modifications may be made which are within the skill of the art. Accordingly, it is intended to be bound only by the following claims, in which:

What is claimed is:

1. A polymer for use in an oral care composition comprising repeating units of the formula:

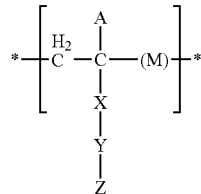

wherein
X is methylene;
Y is a carboxylic group;
Z is the residue of an active material selected from the group consisting of triclosan, thymol and menthol;
A is a carboxylic group; and
M is an optional comonomer;
wherein said polymer releases said active material by aqueous hydrolysis upon administration to an oral cavity.

2. The polymer according to claim 1, which releases a portion of the active material during the time the polymer is present in the mouth of a user, the remainder of the polymer being made available for aqueous hydrolysis thereafter.

3. The polymer according to claim 1 wherein both said comonomer and carboxylic acid groups are attached to the same carbon atom in the main polymer chain.

4. The polymer according to claim 3, wherein the active material can form a 5- or 6-membered anhydride ring with said carboxylic acid group in aqueous solution.

5. The polymer according to claim 1, wherein said active material is present in a side monoester group of itaconic acid.

6. The polymer according to claim 1, wherein said active material is menthol.

7. The polymer according to claim 1, comprising a comonomer.

8. The polymer according to claim 7, wherein said comonomer is a water solubilizing comonomer.

9. The polymer according to claim 7, wherein said comonomer is (meth)acrylic acid, itaconic acid, vinyl acetate, a maleate, a fumarate, vinyl pyrrolidone, vinyl caprolactam, methacrylic acid, vinyl amide, alkyl vinyl ether, maleic anhydride, vinyl sulphonic acid, dimethylaminopropyl methacrylic acid or dimethylaminopropyl methacrylamide.

10. An oral care composition comprising the polymer of claim 7.

11. An oral care composition according to claim 7, wherein the oral care composition is selected from the group consisting of a dentifrice, a denture adhesive, a buccal tape, a mouthwash, a strip, chewing gum, a solution, a gel and a dispersion.

12. An oral care composition comprising the polymer of claim 1.

13. An oral care composition according to claim 12, wherein the oral care composition is selected from the group consisting of a dentifrice, a denture adhesive, a buccal tape, a mouthwash, a strip, chewing gum, a solution, a gel and a dispersion.

14. A water soluble polymer of claim 1 comprising a comonomer wherein said polymer has bioadhesive properties.

* * * * *